US007771348B2

(12) United States Patent
Madsen et al.

(10) Patent No.: US 7,771,348 B2

(45) Date of Patent: Aug. 10, 2010

(54) PERSONAL SONIC MASSAGE DEVICE AND METHOD

(76) Inventors: Alan G. Madsen, 2263 Powhatan Ave., Virginia Beach, VA (US) 23455; Noyal John Alton, Jr., 2408 Eyre Hall Way, Virginia Beach, VA (US) 23456

( * ) Notice: Subject to any disclaimer, the term of this patent is extended or adjusted under 35 U.S.C. 154(b) by 517 days.

(21) Appl. No.: 11/888,289

(22) Filed: Jul. 31, 2007

(65) Prior Publication Data

US 2008/0221489 A1 Sep. 11, 2008

Related U.S. Application Data

(60) Provisional application No. 60/905,000, filed on Mar. 5, 2007.

(51) Int. Cl.
*A61F 5/00* (2006.01)

(52) U.S. Cl. ........................................ 600/38

(58) Field of Classification Search ............ 600/38-41; 128/897, 898; 601/46, 47
See application file for complete search history.

(56) References Cited

U.S. PATENT DOCUMENTS

| | | | | |
|---|---|---|---|---|
| 5,928,170 | A * | 7/1999 | Garrigan | 601/47 |
| 6,277,085 | B1 | 8/2001 | Flynn | |
| 6,770,042 | B2 * | 8/2004 | Lee | 601/47 |
| 7,029,452 | B1 * | 4/2006 | Alton, Jr. | 601/47 |

* cited by examiner

*Primary Examiner*—Samuel G Gilbert
(74) *Attorney, Agent, or Firm*—Peter J. Van Bergen

(57) ABSTRACT

A personal massage system includes first and second audio transducers mounted in and coupled to a housing in a spaced-apart and opposing fashion. The first and second audio transducers are energized to produce corresponding first and second sonic waves that radiate towards one another and interact between the first and second audio transducers.

16 Claims, 4 Drawing Sheets

PERSONAL SONIC MASSAGE DEVICE AND METHOD

ORIGIN OF THE INVENTION

Pursuant to 35 U.S.C. §119 the benefit of priority from provisional application 60/905,000, with a filing date of Mar. 5, 2007, is claimed for this non-provisional application.

FIELD OF THE INVENTION

The invention relates generally to personal massage devices, and more particularly to a personal massage device and method that reproduces two channels of audio signals using two separated audio transducers.

BACKGROUND OF THE INVENTION

A variety of personal massage devices are known in the art. Such devices range from relatively large rolling or kneading types of devices to small, hand-held vibrating devices such as those used for medical treatment or sensual pleasure. These smaller devices typically house a mechanically-reciprocating or eccentrically-rotating driver whose variation in movement is fairly limited so that it is typically governed by a fixed frequency source. If the driver is capable of being responsive to complex waveforms that vary in frequency, the source could be a random or non-random complex signal generator as disclosed in U.S. Pat. No. 6,277,085. However, the range of effects provided by prior art personal massagers may not be sufficient for many users, especially those having decreased sensitivity (e.g., menopausal women).

SUMMARY OF THE INVENTION

Accordingly, it is an object of the present invention to provide a personal massage device.

Another object of the present invention is to provide a personal massage device capable of providing a wide range of effects to thereby improve blood flow and body tissue sensitivity.

Other objects and advantages of the present invention will become more obvious hereinafter in the specification and drawings.

In accordance with the present invention, a personal massage system includes first and second audio transducers mounted in and coupled to a housing in a spaced-apart and opposing fashion. First and second alternating current signals are applied to the first and second audio transducers, respectively. As a result, the first and second audio transducers produce corresponding first and second sonic waves that radiate towards one another and interact between the first and second audio transducers.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
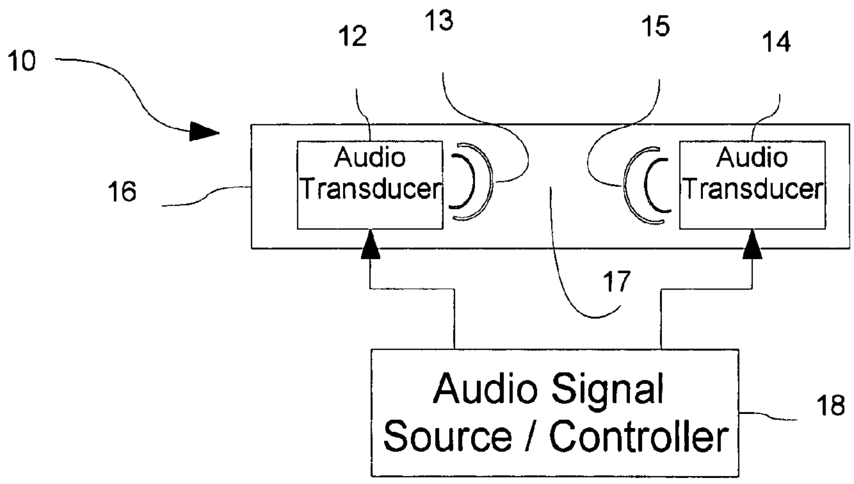
FIG. 1 is a top-level schematic diagram of a personal massage device in accordance with the present invention.

Referring now to the drawings, and more particularly to FIG. 1, a top-level schematic drawing of a personal massage device in accordance with the present invention is shown and is referenced generally by numeral 10. As will become apparent from the following description, the essential and novel features of personal massage device 10 can be adapted to a variety of applications. Indeed, several exemplary applications will be discussed herein. However, it is to be understood that the present invention is not limited to the illustrated examples.

Personal massage device 10 includes (i) two audio transducers 12 and 14 mounted in a housing 16 in a spaced-apart fashion, and (ii) an audio signal source/controller 18 that supplies a unique audio signal to each of audio transducers 12 and 14 so that transducers 12 and 14 define two distinct channels producing two distinct sets of sound waves. In general, audio transducers 12 and 14 radiate sonic waves 13 and 15, respectively, that propagate substantially towards one another when the transducers are energized. A variety of types of audio transducers could be used in the present invention with the choice thereof depending on factors such as size, power/force requirements, cost, etc. Some suitable examples include voice coils and thin-film transducers.

Figure 2A:
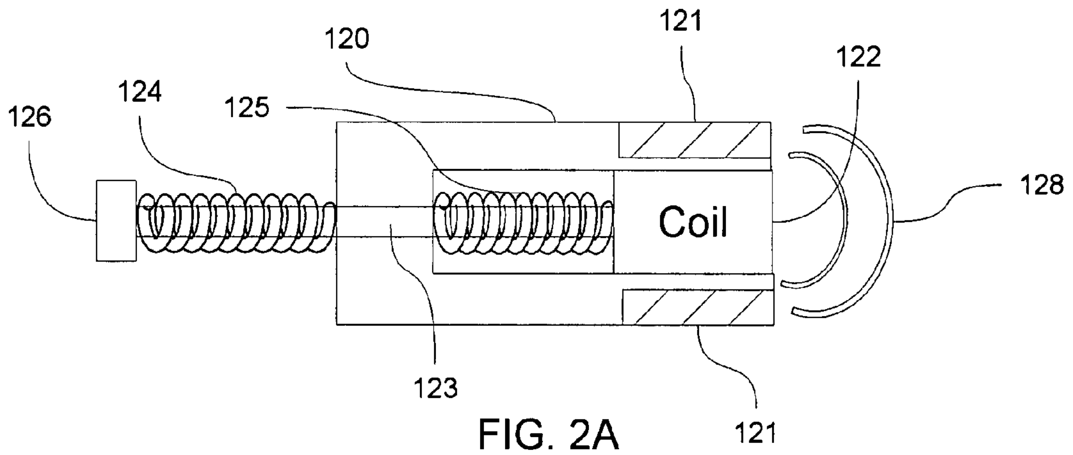
FIG. 2A is a schematic view of a conventional electro-mechanical actuator modified to operate as an audio transducer in the present invention.

For applications/products requiring audio transducers capable of generating relatively large amounts of power/force, commercially-available electro-mechanical actuators can be modified to function as an audio transducer. For example, as illustrated in FIG. 2A, an audio transducer could be constructed using an electro-mechanical actuator defined generally by a housing 120, a stationary magnetic core 121 mounted in housing 120, and a coil 122 coupled to an axially-movable non-magnetic shaft 123 with coil 122 being sized to fit within magnetic core 121. As is well known in the art, as an applied current flows through coil 122, the interaction between magnetic core 121 and coil 122 causes shaft 123/coil 122 to move axially in housing 120. To make this apparatus function as an audio transducer for use in the present invention, springs 124 and 125 are disposed about shaft 123. More specifically, spring 124 is mounted outside of housing 120 and is, for example, captured between housing 120 and a stop 126. Spring 125 is mounted within housing 120 and is held in place by, for example, housing 120 and coil 122. Springs 124 and 125 provide for axially-directed reciprocating motion of shaft 123/coil 122 as coil 122 has an alternating current (e.g., associated with an audio signal) applied thereto. As a result, sonic waves 128 (i.e., analogous to sonic waves 13 or 15) will be produced by such reciprocating movement.

Figure 2B:
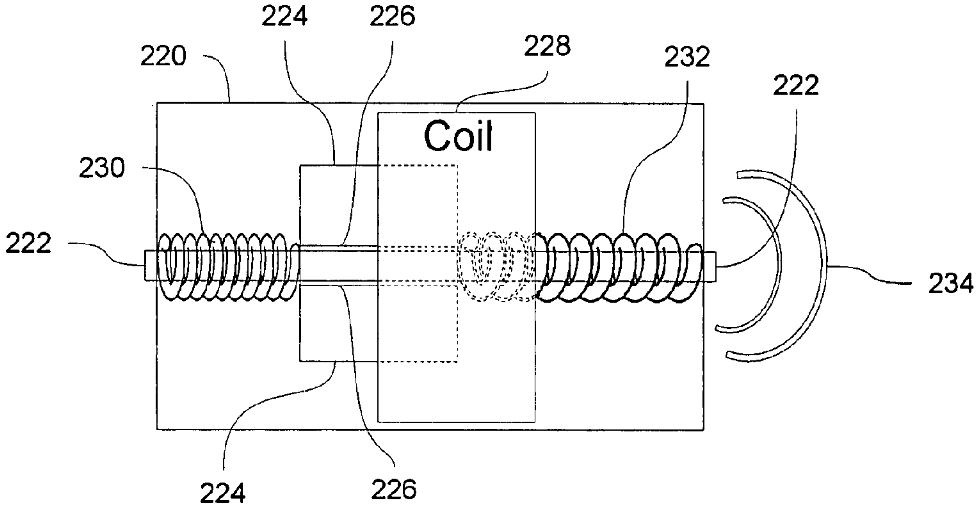
FIG. 2B is a schematic view of another embodiment of an audio transducer in the present invention.

It is to be understood that the present invention is not limited to use with the audio transducer shown in FIG. 2A. Accordingly, by way of example, another audio transducer that can be used in the present invention is illustrated in FIG. 2B. An enclosed housing 220 has a rigid support shaft 222 extending therethrough with either end of shaft 222 being fixed to an opposing side of housing 220. Shaft 222 can be made from a metal or non-metal material provided it is rigid. A ring-shaped magnet 224 is mounted on shaft 222 such that it can slide axially therealong, i.e., in either axial direction. A non-magnetic bushing 226 can be positioned within magnet 224 with bushing 226 being disposed between shaft 222 and magnet 224. The magnet 224/bushing 226 assembly is configured to move "as one" along shaft 222. Note that bushing 226 is required if shaft 222 is magnetic. A coil 228 large enough to allow magnet 224 to pass therethrough is fixed in housing 220. Springs 230 and 232 are disposed about shaft 222 on either side of magnet 224/bushing 226. More specifically, spring 230 is captured between housing 220 and one side of magnet 224/bushing 226, and spring 232 is captured between the other side of magnet 224/bushing 226 and housing 220. Prior to excitement of coil 228 with an alternating current (e.g., associated with an audio signal), each of springs 230 and 232 is in a state of partial compression. The size and/or spring constants of springs 230 and 232 should be such that magnet 224/bushing 226 is axially displaced with respect to the center of coil 228 when coil 228 is not excited. Springs 230 and 232 provide for axially-directed reciprocating motion of magnet 224/bushing 226 on shaft 222 and through coil 228 when coil 228 has an alternating current (e.g., associated with an audio signal) applied thereto. As a result, sonic waves 234 (i.e., analogous to sonic waves 13 or 15) will be produced by such reciprocating movement.

Regardless of the construction of the audio transducers, unique audio signals are supplied to each of transducers 12 and 14. Accordingly, sonic waves 13 and 15 will be defined by a unique frequency at any instant in time. When sonic waves 13 and 15 interact in a zone 17 between transducers 12 and 14, a sonic wave at a third frequency (i.e., different from that of sonic waves 13 and 15) will be generated.

Figure 3:
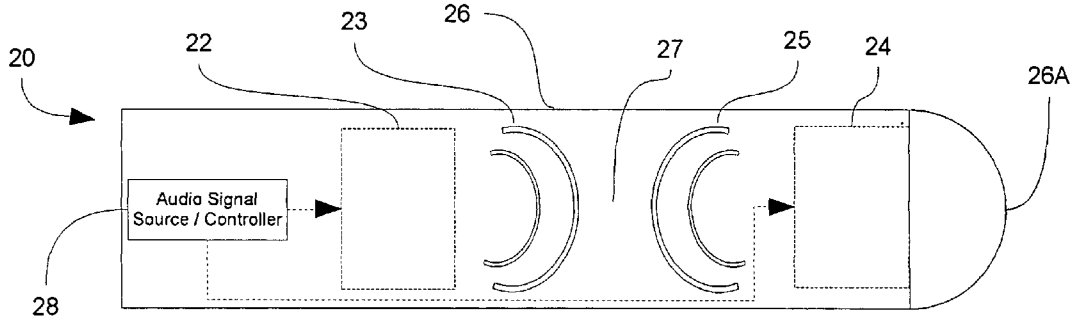
FIG. 3 is a side schematic view of a hand-held housing and audio transducer arrangement for the personal sonic massage device when it is configured for female stimulation in accordance with an embodiment of the present invention.

Referring now to FIG. 3, one embodiment of a personal massage device in accordance with the present invention is shown and is referenced by numeral 20. Audio transducers 22 and 24 are mounted in a housing 26 that is shaped and sized to resemble a penis with a closed rounded tip 26A. Housing 26 can be a straight cylindrical shape (as shown) or arcuately-shaped without departing from the scope of the present invention. The exterior surface of housing 26 can be hard or supple, or smooth, ribbed or dimpled, etc., without departing from the scope of the present invention.

In general, audio transducer 24 is mounted in housing 26 near its rounded tip 26A while audio transducer 22 is mounted in housing 26 at a position that is axially displaced from rounded tip 26A. The position of audio transducer 22 should be such that when housing 26 is inserted into a woman's vagina so that rounded tip 26A is near or in contact with the woman's cervix, audio transducer 22 is positioned near the paraurethral gland of the urethral sponge (i.e., also referred to as the Grafenberg spot or "G-spot").

In most cases, when housing 26 is sized to resemble an average penis of approximately 6 inches, audio transducer 22 is positioned at a location that is approximately 3-5 inches away from rounded tip 26A. However, the present invention is not limited to such positioning. Indeed, the construction of massage device 20 could provide for user-adjustable positioning of one or both of audio transducers 22 and 24 in order to satisfy the needs of a particular user.

As was the case with audio transducers 12 and 14, each of audio transducers 22 and 24 is a transducer device that generates sonic waves in accordance with an applied source signal and directs the sonic waves substantially axially along housing 26. That is, in the illustrated embodiment, when audio transducer 22 is energized, sonic waves 23 are generated within housing 26 with most of the energy associated therewith radiating axially in housing 26 towards transducer 24. Sonic waves 23 are also coupled into housing 26 and are ultimately radiated radially outward from housing 26. When audio transducer 24 is energized, sonic waves 25 are generated within housing 26 with most of the energy associated therewith radiating axially within housing 26 towards transducer 22. Sonic waves 25 are also coupled into housing 26 and are ultimately radiated outward therefrom. Sonic waves 23 and 25 interact in a zone 27 within housing 26 between transducers 22 and 24 with the interacting sonic waves forming another sonic wave having a frequency that is different from that of sonic waves 23 and 25. The third sonic wave is also coupled into housing 26 and radiates outward therefrom.

The actual mounting relationship between audio transducers 22/24 and housing 26 can be achieved by a variety of constructions without departing from the scope of the present invention. For example, audio transducers 22/24 could be mounted directly to the inside of housing 26. Another option is to mount audio transducers 22/24 in a hollow tube (not shown), and then insert the resulting assembly into housing 26 or mold housing 26 onto such an assembly.

Figure 4:
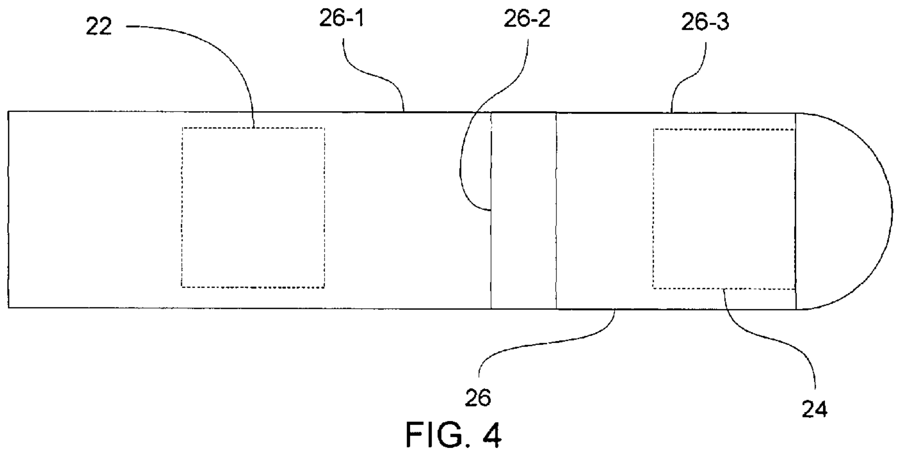
FIG. 4 is an isolated side view of a sectioned housing that can be used to provide an enhanced stereo massaging effect in accordance with the present invention.

Housing 26 can be constructed from one type of material all along its length, or could comprise acoustically different types of materials along its length to provide some acoustic isolation between audio transducers 22 and 24. For example, as shown in FIG. 4, housing 26 can be made from sections 26-1, 26-2 and 26-3, where sections 26-1 and 26-3 house audio transducers 22 and 24, respectively, and section 26-2 couples section 26-1 to section 26-3. If section 26-2 is defined by a material that is acoustically mismatched to sections 26-1 and 26-3, the sonic waves produced by audio transducers 22 and 24 can be isolated from one another as they radiate from housing 26 to thereby provide an enhanced stereo massage effect.

Regardless of the particular construction of transducers 22/24 and housing 26, each of audio transducers 22 and 24 is energized with an independent and unique audio signal from an audio signal source/controller 28 (FIG. 3) that can comprise one or more functional units without departing from the scope of the present invention. For example, source/controller 28 could be a completely self-contained system that generates or stores audio material (e.g., "read only memory" or ROM storing pre-recorded music, specially-designed waveforms, or a combination of these two), separates the audio material into distinct frequency bands and channels, and appropriately amplifies the audio material prior to its application to audio transducers 22 and 24. For simplicity and/or ease of use, source/controller 28 can be mounted within housing 26 as shown.

The audio material can be frequency filtered (e.g., low-pass, high-pass, bandpass, etc.) prior to being applied to audio transducers 22 and 24. For example, it may be desirable to energize transducers 22 and 24 with only low frequency (e.g., 50 Hz or less) audio signals. Thus, if the audio material consisted of a pre-recorded stereo music program, the lower frequencies can be filtered out with the left and right channels thereof being applied to transducers 22 and 24, respectively. The higher frequencies associated with the pre-recorded stereo music program can then simultaneously be reproduced for the user's audible enjoyment. In this mode of operation, a user will be massaged in accordance with the rhythms being heard. Accordingly, source/controller 28 can include loudspeaker(s) (not shown) or a jack (not shown) that allows a set of headphones to be coupled thereto. To accommodate this scenario, source/controller 28 would include a cross-over network to provide for such audio material division/separation. As mentioned above, the audio material can be stored by source/controller 28 or could be provided thereto by an external device (e.g., CD player, MP3 player, flash memory, etc.) without departing from the scope of the present invention.

Figure 5:
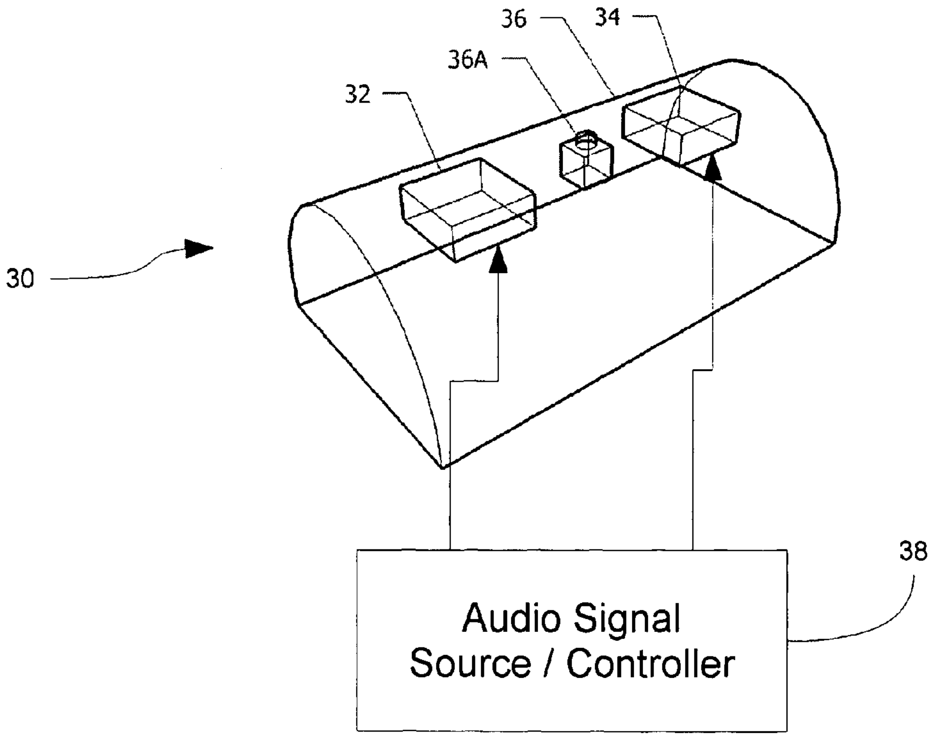
FIG. 5 is a perspective view of a straddle-type of housing and audio transducer arrangement for the personal sonic massage device when it is configured for female stimulation in accordance with another embodiment of the present invention.

Another embodiment of a personal massage device in accordance with the present invention is illustrated in FIG. 5 and is referenced generally by numeral 30. Personal massage device 30 has a housing 36 sized and shaped to allow a user thereof to sit thereon and straddle housing 36. Materials used for housing 36 as well as the contours of the outer surface thereof can be similar to that described above for housing 26. Disposed within housing 36 are audio transducers 32 and 34 that are similar in design to the audio transducers previously described herein. Transducers 32 and 34 can be mounted directly in housing 36 or within a support mandrel (not shown) that can be positioned in housing 36. Housing 36 can also include a mount 36A positioned between transducers 32 and 34. Mount 36A is any structure that can be used to support the previously-described housing 26 of massage device 20 (not shown in FIG. 6) in a vertical orientation (i.e., extending vertically up from housing 36). In this way, a user can straddle and sit on housing 36 to receive external stimulation from transducers 32 and 34 while simultaneously receiving internal stimulation from transducers 22 and 24.

Similar to the previously-described embodiments, each of transducers 32 and 34 is energized by a unique audio signal program provided thereto by an audio signal source/controller 38. In terms of providing sensual pleasure, it may be necessary for transducers 32 and 34 to be larger and more powerful than transducers 22 and 24.

For each embodiment of the present invention, each of the audio signals supplied to each of the audio transducers is unique. Since the audio transducers are spatially separated (and can be acoustically isolated in their housing), each embodiment of the personal massage device of the present invention produces a stereo massage experience. Furthermore, the audio signal programming can be controlled so that the sonic waves radiating from the housing generate a sensation of movement by the affected body tissue without any actual relative movement between the user's body tissue and the massage device's housing. For example, the audio signals can be designed to generate a phasing Doppler effect that generates a third frequency as the sonic waves from the transducers interact in a zone between the transducers. That is, at any given instant in time, the third frequency is the sum or difference between the frequencies being generated by the two audio transducers.

Figure 6:
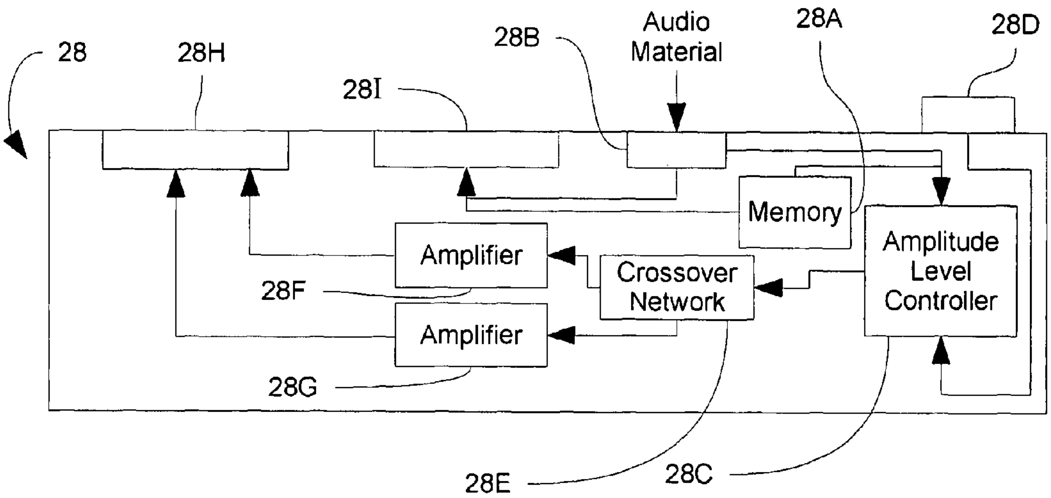
FIG. 6 is a functional block diagram of an embodiment of an audio signal source/controller used to drive the audio transducers in the present invention.

By way of a non-limiting example, an embodiment of an audio signal source/controller (e.g., source/controller 28) is shown in FIG. 6. Audio material having both a specially-designed massage program (e.g., waveforms at low frequencies) and a musical program (e.g., at frequencies above those used for the massage program) is stored in a memory 28A (e.g., ROM) or applied from an external source to an input port 28B. (Note that a low-frequency massage program could also be derived from the low-frequency portion of a pre-recorded musical program.) An amplitude level controller 28C sets the amplitude of the audio material in accordance with a user input provided through a user control 28D. The audio material is separated into its channels by a cross-over network 28E. The two unique channels of the audio material are amplified by amplifier(s) 28F and 28G, and then supplied to an output port 28H. The present invention's audio transducers can be hardwired to output port 28H with each of the two transducers receiving the audio material amplified by a corresponding one of amplifiers 28F and 28G. Alternatively, output port 28H could be a wireless port that wirelessly transmits the massage program to the audio transducers. Of course, this would require wireless reception electronics in the housing that supports the audio transducers. The audio material to include the musical program is also made available at an output port 28I (e.g., headphone jack, loudspeaker jack, wireless port, etc.).

Figure 7:
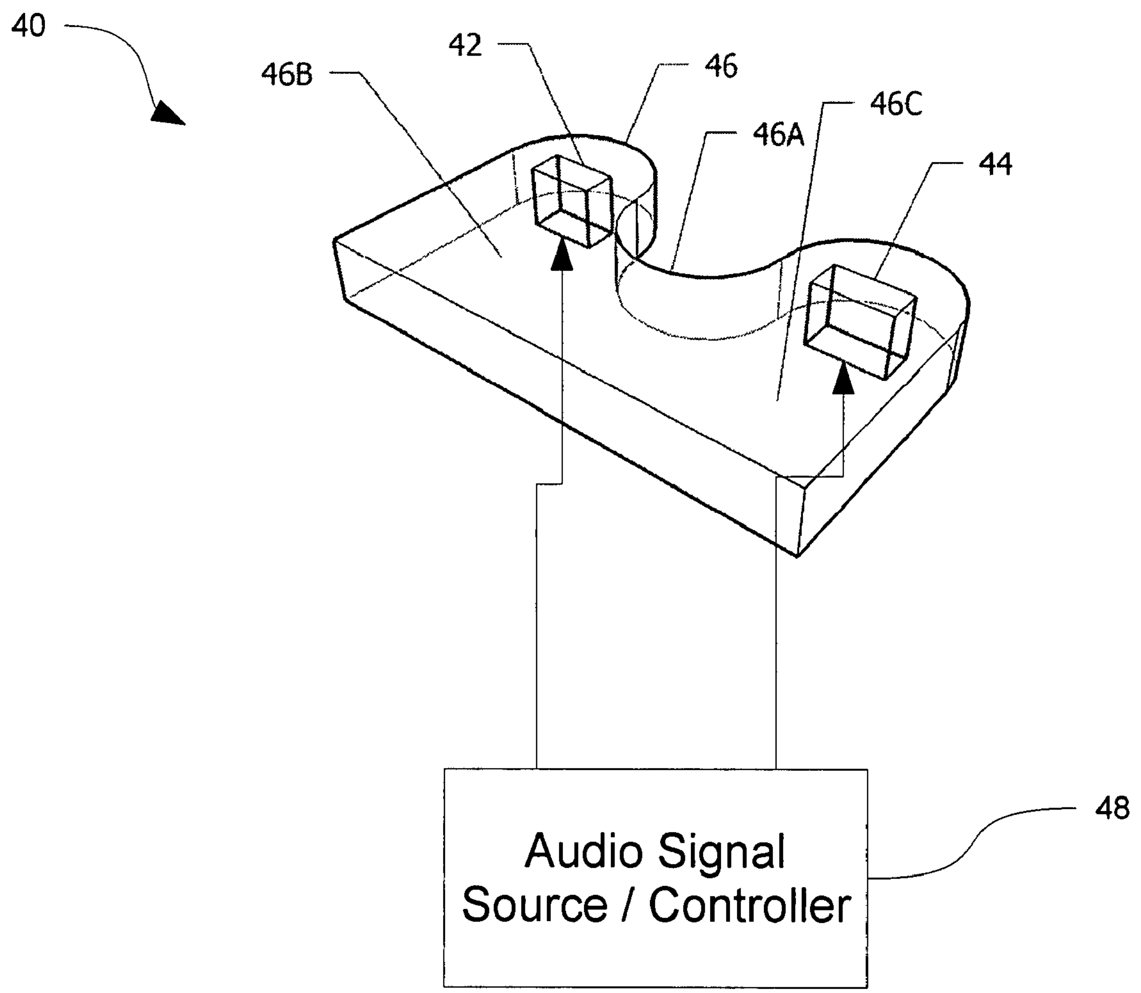
FIG. 7 is a perspective view of a cradle-shaped housing and audio transducer arrangement for the personal sonic massage device when it is configured for stimulation of one's wrist in accordance with another embodiment of the present invention.

The present invention is not limited to personal massage devices used for sensual pleasure. That is, in general, the present invention can be adapted to a variety of massage applications. For example, FIG. 7 illustrates another personal massage device 40 that can be used to treat Repetitive Stress Injury (RSI) associated with prolonged use of a computer mouse. Massage device 40 includes (i) audio transducers 42 and 44 mounted in a housing 46, and (ii) an audio signal source/controller 48 that supplies the requisite audio material to transducers 42 and 44. Housing 46 is generally cradle-shaped to allow a user to rest his wrist in the housing's central section 46A so that the housing's opposing side sections 46B and 46C are disposed on either side of the wrist. Transducer 42 is mounted in side section 46B such that it will radiate sound waves towards one side of the wrist, and transducer 44 is mounted in section 46C such that it will radiate sound waves towards the other side of the wrist. Source/controller 48 supplies a massage program (e.g., specially-designed waveforms, pre-recorded music, or a combination of these two) to transducers 42 and 44. Since this embodiment would typically be used in proximity to a computer, source/controller 48 could be realized by a combination of the computer (not shown) and software stored thereon.

Although the invention has been described relative to a specific embodiment thereof, there are numerous variations and modifications that will be readily apparent to those skilled in the art in light of the above teachings. For example, some applications might benefit from the use of three or more audio transducers to provide a "surround sound" massage effect. It is therefore to be understood that, within the scope of the appended claims, the invention may be practiced other than as specifically described.

What is claimed as new and desired to be secured by Letters Patent of the United States is:

1. A personal massage system comprising:
a housing shaped like a penis;
first and second audio transducers mounted in and coupled to said housing in a spaced-apart and opposing fashion; and
means for applying unique first and second alternating current signals to said first and second audio transducers, respectively, wherein said first and second audio transducers produce corresponding first and second sonic waves that radiate towards one another and interact between said first and second audio transducers within said housing.

2. A personal massage system as in claim 1 wherein an exterior surface of said housing has a texture that is selected from the group consisting of smooth, ribbed and dimpled.

3. A personal massage system as in claim 1 wherein an exterior surface of said housing is hard.

4. A personal massage system as in claim 1 wherein an exterior surface of said housing is supple.

5. A personal massage system as in claim 1 wherein each of said first and second audio transducers comprises an electro-mechanical actuator configured for reciprocating motion when actuated by one of said first and second alternating current signals.

6. A personal massage system comprising:

a housing shaped like a penis having a rounded tip formed at one end thereof and having a base defined at an opposing end thereof;

first means for generating first sonic waves, said first means mounted in said housing in proximity to said rounded tip and positioned to radiate said first sonic waves substantially towards said base; and second means for generating second sonic waves, said second means mounted in said housing further from said rounded tip than said first means and spaced apart therefrom, said second means positioned in said housing to radiate said second sonic waves substantially towards said rounded tip wherein said first and second sonic waves interact with one another within said housing between said first and second means.

7. A personal massage system as in claim 6 wherein an exterior surface of said housing has a texture that is selected from the group consisting of smooth, ribbed and dimpled.

8. A personal massage system as in claim 6 wherein an exterior surface of said housing is hard.

9. A personal massage system as in claim 6 wherein an exterior surface of said housing is supple.

10. A personal massage system as in claim 6 wherein each of said first and second audio transducers comprises an electro-mechanical actuator configured for reciprocating motion when actuated by an alternating current signal.

11. A personal massage system comprising:

a housing shaped like a penis having a rounded tip formed at one end thereof and having a base defined at an opposing end thereof;

first means for generating first sonic, waves in response to a first alternating current signal, said first means mounted in said housing in proximity to said rounded tip and positioned to radiate said first sonic waves substantially towards said base;

second means for generating second sonic waves in response to a second alternating current signal, said second means mounted in said housing further from said rounded tip than said first means and spaced apart therefrom, said second means positioned in said housing to radiate said second sonic waves substantially towards said rounded tip wherein said first and second sonic waves interact with one another within said housing between said first and second means; and third means mounted in said housing for supplying said first alternating current signal to said first means and said second alternating current signal to said second means, wherein said first alternating current signal is different than said second alternating current signal.

12. A personal massage system as in claim 11 wherein said third means includes read only memory (ROM) for storing data indicative of said first alternating current signal and said second alternating current signal.

13. A personal massage system as in claim 11 wherein an exterior surface of said housing has a texture that is selected from the group consisting of smooth, ribbed and dimpled.

14. A personal massage system as in claim 11 wherein an exterior surface of said housing is hard.

15. A personal massage system as in claim 11 wherein an exterior surface of said housing is supple.

16. A personal massage system as in claim 11 wherein each of said first and second means comprises an electro-mechanical actuator configured for reciprocating motion when actuated by one of said first and second alternating current signals.

* * * * *